United States Patent [19]

Frey et al.

[11] Patent Number: 6,054,573
[45] Date of Patent: Apr. 25, 2000

[54] HIGHLY INFECTIOUS RUBELLA VIRUS CLONES AND METHODS OF PRODUCTION

[75] Inventors: Teryl K. Frey, Atlanta; Konstantin Pougatchev, Chamblee; Emily S. Abernathy, Atlanta, all of Ga.

[73] Assignee: Georgia State University, Atlanta, Ga.

[21] Appl. No.: 08/999,733

[22] Filed: Sep. 2, 1997

Related U.S. Application Data

[63] Continuation-in-part of application No. 08/459,041, Jun. 2, 1995, Pat. No. 5,663,065, which is a continuation-in-part of application No. 08/093,453, Jul. 19, 1993, Pat. No. 5,439,814, which is a continuation of application No. 07/722,334, Jun. 28, 1991, abandoned.

[51] Int. Cl.$^7$ .................................................. C12N 15/40
[52] U.S. Cl. ................................... 536/23.72; 435/235.1; 435/320.1
[58] Field of Search .......................... 435/320.1, 235.1, 435/471, 472, 475; 536/23.72

[56] References Cited

U.S. PATENT DOCUMENTS 5,439,814   8/1995   Frey et al. .
5,663,065   9/1997   Frey et al. .

OTHER PUBLICATIONS

Pugachev, K.V. et al. Journal of Virology 71:562–568, Jan. 1997.
Wang et al. Journal of Virology 68(6): 3550–3557, Jun. 1994.
Ahlquist et al., *J. Mol. Biol.* 172: 369–383 (1984).
Ahlquist et al., *Mol. Cell. Biol.* 4: 2876–2882 (1984).
Ahlquist et al., *Proc. Nat'l Acad. Sci.* USA 91: 7066–7070 (1984).
Ballart et al., *EMBO J* 10(11): 3558 (1991).
Callahan et al., *Proc. Nat'l Acad. Sci.* USA 82: 732–736 (1985).
Clarke et al., *Nucleic Acids Res.* 15: 3041–3057 (1987).
Cotlier et al., *Nature* 217: 38–40 (1968).
Cunningham et al., *J. Infect. Dis.* 151:638–645 (1985).
Davis et al., *Virology* 171: 189–204 (1989).
Dominguez et al., *Virology* 177: 225–238 (1990).
Frey et al., *Gene* 62: 85–99 (1988).
Frey et al., *Virol.* 168: 191–194 (1989).
Frey et al., *Virology* 154: 228–232 (1986).
Green et al., *J. Virol.* 57: 893–898 (1986).
Hovi et al., *Virology* 42: 1–8 (1970).
Kono et al., *The Lancet* :343–347 (Feb. 15, 1969).
London et al., *Nature* 226: 172–173 (1970).
London et al., *Symp. Series Immunobiol. Standard.* 11: 121–124 (1969).
Mizutani et al., *J. Virol.* 56: 628–632 (1985).
Nakhasi et al., *J. Biol. Chem.* 261: 16616–16621 (1986).
Niesters et al., *J. Virol.* 64: 4162–4168 (1990).
Oh et al., *J. Mol. Biol.* 168:1–15 (1983).
Oker–blom et al., *J. Virol.* 46: 964–973 (1983).
Oker–Blom, *J. Virol.* 51: 354–358 (1984).
Rice et al., *Virology* 61: 3809–3819 (1987).
Takkinen et al., *J. gen. Virol.* 69: 603–612 (1988).
Vidgren et al., *J. Gen. Virol.* 68: 2347–2357 (1987).
Wang et al., *J. Virol.* 68(6): 3550–3557 (1994).
Waxham et al., *Virology* 126: 194–203 (1983).
Waxham et al., *Virology* 143: 153–165 (1985).
Weibel et al., *Proc. Soc. Exp. Biol. Med.* 165: 44–45 (1980).
Zheng et al., *Gene* 82: 343–349 (1989).
Chantler et al., *Intervirology* (Switzerland) 36(4): 225–36 (1993) (abstract).
Frenkel et al., *Arch Pediatr. Adolesc. Med.* 148(1): 57–60 (1994) (abstract).
Mitchell et al., *Arch. Intern Med* 153(19): 2268–74 (1993) (abstract).
Mauracher et al., *Journal of Immunology* 151: 2041–2049 (1993).
Hobman et al., *Virology* 202: 574–585 (1994).
Zheng et al., *Gene* 82: 343–349 (1988).
Frey, et al., *Journal of Infectious Diseases* 168: 854–864 (1993).
Geiger et al., *J. Med. Vir.* 47: 442–444 (1995).
Barnes, W. M., *Proc. Natl. Acad. Sci.* USA 91: 2216–2220 (1994).
Cheng et al., *Proc. Natl. Acad. Sci.* USA 91: 5695–5699 (1994).

*Primary Examiner*—Mary E. Mosher
*Attorney, Agent, or Firm*—Jones & Askew, LLP

[57] ABSTRACT

Highly infectious rubella virus cDNA clones that are chimeric constructs of an infectious cDNA clone having a low specific infectivity and nucleic acid molecule fragments from a second rubella virus genome, wherein portions of the nucleotide sequence of the infectious cDNA clone having low specific infectivity have been replaced with the corresponding cDNA fragments derived from the second rubella virus genome.

2 Claims, 3 Drawing Sheets

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 9759 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
CAATGGAAGC TATCGGACCT CGCTTAGGAC TCCCATTCCC ATGGAGAAAC TCCTAGATGA      60

GGTTCTTGCC CCCGGTGGGC CTTATAACTT AACCGTCGGC AGTTGGGTAA GAGACCACGT     120

CCGATCAATT GTCGAGGGCG CGTGGGAAGT GCGCGATGTT GTTACCGCTG CCCAAAAGCG     180

GGCCATCGTA GCCGTGATAC CCAGACCTGT GTTCACGCAG ATGCAGGTCA GTGATCACCC     240

AGCACTCCAC GCAATTTCGC GGTATACCCG CCGCCATTGG ATCGAGTGGG GCCCTAAAGA     300

AGCCCTACAC GTCCTCATCG ACCCAAGCCC GGGCCTGCTC CGCGAGGTCG CTCGCGTTGA     360

GCGCCGCTGG GTCGCACTGT GCCTCCACAG GACGGCACGC AAACTCGCCA CCGCCCTGGC     420

CGAGACGGCC AGCGAGGCGT GGCACGCTGA CTACGTGTGC GCGCTGCGTG GCGCACCGAG     480
```

-continued

```
CGGCCCCTTC TACGTCCACC CTGAGGACGT CCCGCACGGC GGTCGCGCCG TGGCGGACAG        540
ATGCTTGCTC TACTACACAC CCATGCAGAT GTGCGAGCTG ATGCGTACCA TTGACGCCAC        600
CCTGCTCGTG GCGGTTGACT TGTGGCCGGT CGCCCTTGCG GCCCACGTCG GCGACGACTG        660
GGACGACCTG GGCATTGCCT GGCATCTCGA CCATGACGGC GGTTGCCCCG CCGATTGCCG        720
CGGAGCCGGC GCTGGGCCCA CGCCCGGCTA CACCCGCCCC TGCACCACAC GCATCTACCA        780
AGTCCTGCCG GACACCGCCC ACCCCGGGCG CCTCTACCGG TGCGGGCCCC GCCTGTGGAC        840
GCGCGATTGC GCCGTGGCCG AACTCTCATG GGAGGTTGCC CAACACTGCG GGCACCAGGC        900
GCGCGTGCGC GCCGTGCGAT GCACCCTCCC TATCCGCCAC GTGCGCAGCC TCCAACCCAG        960
CGCGCGGGTC CGACTCCCGG ACCTCGTCCA TCTCGCCGAG GTGGGCCGGT GGCGGTGGTT       1020
CAGCCTCCCC CGCCCCGTGT TCCAGCGCAT GCTGTCCTAC TGCAAGACCC TGAGCCCCGA       1080
CGCGTACTAC AGCGAGCGCG TGTTCAAGTT CAAGAACGCC CTGTGCCACA GCATCACGCT       1140
CGCGGGCAAT GTGCTGCAAG AGGGGTGGAA GGGCACGTGC GCCGAGGAAG ACGCGCTGTG       1200
CGCATACGTA GCCTTCCGCG CGTGGCAGTC TAACGCCAGG TTGGCGGGGA TTATGAAAGG       1260
CGCGAAGCGC TGCGCCGCCG ACTCTTTGAG CGTGGCCGGC TGGCTGGACA CCATTTGGGA       1320
CGCCATTAAG CGGTTCCTCG GTAGCGTGCC CCTCGCCGAG CGCATGGAGG AGTGGGAACA       1380
GGACGCCGCG GTCGCCGCCT TCGACCGCGG CCCCCTCGAG GACGGCGGGC GCCACTTGGA       1440
CACCGTGCAA CCCCCAAAAT CGCCGCCCCG CCCTGAGATC GCCGCGACCT GGATCGTCCA       1500
CGCAGCCAGC GAAGACCGCC ATTGCGCGTG CGCTCCCCGC TGCGACGTCC CGCGCGAACG       1560
TCCTTCCGCG CCCGCCGGCC AGCCGGATGA CGAGGCGCTC ATCCCGCCGT GGCTGTTCGC       1620
CGAGCGCCGT GCCCTCCGCT GCCGCGAGTG GGATTTCGAG GCTCTCCGCG CGCGCGCCGA       1680
TACGGCGGCC GCGCCCGCCC CGCCGGCTCC ACGCCCCGCG CGGTACCCCA CCGTGCTCTA       1740
CCGCCACCCC GCCCACCACG GCCCGTGGCT CACCCTTGAC GAGCCGGGCG AGGCTGACGC       1800
GGCCCTGGTC TTATGCGACC CACTTGGCCA GCCGCTCCGG GGCCCTGAAC GCCACTTCGC       1860
CGCCGGCGCG CATATGTGCG CGCAGGCGCG GGGGCTCCAG GCTTTTGTCC GTGTCGTGCC       1920
TCCACCCGAG CGCCCCTGGG CCGACGGGGG CGCCAGAGCG TGGGCGAAGT TCTTCCGCGG       1980
CTGCGCCTGG GCGCAGCGCT TGCTCGGCGA GCCAGCAGTT ATGCACCTCC CATACACCGA       2040
TGGCGACGTG CCACAGCTGA TCGCACTGGC TTTGCGCACG CTGGCCCAAC AGGGGGCCGC       2100
CTTGGCACTC TCGGTGCGTG ACCTGCCCGG GGGTGCAGCG TTCGACGCAA ACGCGGTCAC       2160
CGCCGCCGTG CGCGCTGGCC CCCGCCAGTC CGCGGCCGCG TCACCGCCAC CCGGCGACCC       2220
CCCGCCGCCG CGCCGCGCAC GGCGATCGCA ACGGCACTCG GACGCTCGCG GCACTCCGCC       2280
CCCCGCGCCT GCGCGCGACC CGCCGCCGCC CGCCCCAGC  CCGCCCGCGC CACCCCGCGC       2340
TGGTGACCCG GTCCCTCCCA TTCCCGCGGG GCCGGCGGAT CGCGCGCGTG ACGCCGAGCT       2400
GGAGGTCGCC TGCGAGCCGA GCGGCCCCCC CACGTCAACC AGGGCAGACC CAGACAGCGA       2460
CATCGTTGAA AGTTACGCCC GCGCCGCCGG ACCCGTGCAC CTCCGAGTCC GCGACATCAT       2520
GGACCCACCG CCCGGCTGCA AGGTCGTGGT CAACGCCGCC AACGAGGGGC TACTGGCCGG       2580
CTCTGGCGTG TGCGGTGCCA TCTTTGCCAA CGCCACGGCG GCCCTCGCTG CAAACTGCCG       2640
GCGCCTCGCC CCATGCCCCA CCGGCGAGGC AGTGGCGACA CCCGGCCACG GCTGCGGGTA       2700
CACCCACATC ATCCACGCCG TCGCGCCGCG GCGTCCTCGG GACCCCGCCG CCCTCGAGGA       2760
GGGCGAAGCG CTGCTCGAGC GCGCCTACCG CAGCATCGTC GCGCTAGCCG CCGCGCGTCG       2820
GTGGGCGTGT GTCGCGTGCC CCCTCCTCGG CGCTGGCGTC TACGGCTGGT CTGCTGCGGA       2880
```

```
GTCCCTCCGA GCCGCGCTCG CGGCTACGCG CACCGAGCCC GTCGAGCGCG TGAGCCTGCA    2940

CATCTGCCAC CCCGACCGCG CCACGCTGAC GCACGCCTCC GTGCTCGTCG GCGCGGGGCT    3000

CGCTGCCAGG CGCGTCAGTC CTCCTCCGAC CGAGCCCCTC GCATCTTGCC CCGCCGGTGA    3060

CCCGGGCCGA CCGGCTCAGC GCAGCGCGTC GCCCCCAGCG ACCCCCCTTG GGGATGCCAC    3120

CGCGCCCGAG CCCCGCGGAT GCCAGGGGTG CGAACTCTGC CGGTACACGC GCGTCACCAA    3180

TGACCGCGCC TATGTCAACC TGTGGCTCGA GCGCGACCGC GGCGCCACCA GCTGGGCCAT    3240

GCGCATTCCC GAGGTGGTTG TCTACGGGCC GGAGCACCTC GCCACGCATT TTCCATTAAA    3300

CCACTACAGT GTGCTCAAGC CCGCGGAGGT CAGGCCCCCG CGAGGCATGT GCGGGAGTGA    3360

CATGTGGCGC TGCCGCGGCT GGCATGGCAT GCCGCAGGTG CGGTGCACCC CCTCCAACGC    3420

TCACGCCGCC CTGTGCCGCA CAGGCGTGCC CCCTCGGGCG AGCACGCGAG GCGGCGAGCT    3480

AGACCCAAAC ACCTGCTGGC TCCGCGCCGC CGCCAACGTT GCGCAGGCTG CGCGCGCCTG    3540

CGGCGCCTAC ACGAGTGCCG GGTGCCCCAA GTGCGCCTAC GGCCGCGCCC TGAGCGAAGC    3600

CCGCACTCAT GAGGACTTCG CCGCGCTGAG CCAGCGGTGG AGCGCGAGCC ACGCCGATGC    3660

CTCCCCTGAC GGCACCGGAG ATCCCCTCGA CCCCCTGATG GAGACCGTGG GATGCGCCTG    3720

TTCGCGCGTG TGGGTCGGCT CCGAGCATGA GGCCCCGCCC GACCACCTCC TGGTGTCCCT    3780

TCACCGTGCC CCAAATGGTC CGTGGGGCGT AGTGCTCGAG GTGCGTGCGC GCCCCGAGGG    3840

GGGCAACCCC ACCGGCCACT TCGTCTGCGC GGTCGGCGGC GGCCCACGCC GCGTCTCGGA    3900

CCGCCCCCAC CTCTGGCTTG CGGTCCCCCT GTCTCGGGGC GGTGGCACCT GTGCCGCGAC    3960

CGACGAGGGG CTGGCCCAGG CGTACTACGA CGACCTCGAG GTGCGCCGCC TCGGGGATGA    4020

CGCCATGGCC CGGGCGGCCC TCGCATCAGT CCAACGCCCT CGCAAAGGCC CTTACAATAT    4080

CAGGGTATGG AACATGGCCG CAGGCGCTGG CAAGACTACC CGCATCCTCG CTGCCTTCAC    4140

GCGCGAAGAC CTTTACGTCT GCCCCACCAA TGCGCTCCTG CACGAGATCC AGGCCAAACT    4200

CCGCGCGCGC GATATCGACA TCAAGAACGC CGCCACCTAC GAGCGCCGGC TGACGAAACC    4260

GCTCGCCGCC TACCGCCGCA TCTACATCGA TGAGGCGTTC ACTCTCGGCG GCGAGTACTG    4320

CGCGTTCGTT GCCAGCCAAA CCACCGCGGA GGTGATCTGC GTCGGTGATC GGGACCAGTG    4380

CGGCCCACAC TACGCCAATA ACTGCCGCAC CCCCGTCCCT GACCGCTGGC CTACCGAGCG    4440

CTCGCGCCAC ACTTGGCGCT TCCCCGACTG CTGGGCGGCC CGCCTGCGCG CGGGGCTCGA    4500

TTATGACATC GAGGGCGAGC GCACCGGCAC CTTCGCCTGC AACCTTTGGG ACGGCCGCCA    4560

GGTCGACCTT CACCTCGCCT TCTCGCGCGA AACCGTGCGC CGCCTTCACG AGGCTGGCAT    4620

ACGCGCATAC ACCGTGCGCG AGGCCCAGGG TATGAGCGTC GGCACCGCCT GCATCCATGT    4680

AGGCAGAGAC GGCACGGACG TTGCCCTGGC GCTGACACGC GACCTCGCCA TCGTCAGCCT    4740

GACCCGGGCC TCCGACGCAC TCTACCTCCA CGAGCTCGAG GACGGCTCAC TGCGCGCTGC    4800

GGGGCTCAGC GCGTTCCTCG ACGCCGGGGC ACTGGCGGAG CTCAAGGAGG TTCCCGCTGG    4860

CATTGACCGC GTTGTCGCCG TCGAGCAGGC ACCACCACCG TTGCCGCCCG CCGACGGCAT    4920

CCCCGAGGCC AAGACGTGCC GCCCTTCTG CCCCCGCACT CTGGAGGAGC TCGTCTTCGG    4980

CCGTGCCGGC CACCCCCATT ACGCGGACCT CAACCGCGTG ACTGAGGGCG AACGAGAAGT    5040

GCGGTACATG CGCATCTCGC GTCACCTGCT CAACAAGAAT CACACCGAGA TGCCCGGAAC    5100

GGAACGCGTT CTCAGTGCCG TTTCGCCGTG CGGCTACCGC GCGGGCGAGG ATGGGTCGAC    5160

CCTCCGCACT GCTGTGGCCC GCCAGCACCC GCGCCCTTTT CGCCAGATCC CACCCCCGCG    5220
```

-continued

```
CGTCACTGCT GGGGTCGCCC AGGAGTGGCG CATGACGTAC TTGCGGGAAC GGATCGACCT     5280

CACTGATGTC TACACGCAGA TGGGCGTGGC CGCGCGGGAG CTCACCGACC GCTACGCGCG     5340

CCGCTATCCT GAGATCTTCG CCGGCATGTG TACCGCCCAG AGCCTGAGCG TCCCCGCCTT     5400

CCTCAAAGCC ACCTTGAAGT GCGTAGACGC CGCCCTCGGC CCCAGGGACA CCGAGGACTG     5460

CCACGCCGCT CAGGGAAAG CCGGCCTTGA GATCCGGGCG TGGGCCAAGG AGTGGGTTCA      5520

GGTTATGTCC CCGCATTTCC GCGCGATCCA GAAGATCATC ATGCGCGCCT TGCGCCCGCA     5580

ATTCCTTGTG GCCGCTGGCC ATACGGAGCC CGAGGTCGAT GCGTGGTGGC AGGCCCATTA     5640

CACCACCAAC GCCATCGAGG TCGACTTCAC TGAGTTCGAC ATGAACCAGA CCCTCGCTAC     5700

TCGGACGTC GAGCTCGAGA TTAGCGCCGC TCTCTTGGGC CTCCCTTGCG CCGAAGACTA      5760

CCGCGCGCTC CGCGCCGGCA GCTACTGCAC CCTGCGCGAA CTGGGCTCCA CTGAGACCGG     5820

CTGCGAGCGC ACAAGCGGCG AGCCCGCCAC GCTGCTGCAC AACACCACCG TGGCCATGTG     5880

CATGGCCATG CGCATGGTCC CCAAAGGCGT GCGCTGGGCC GGGATTTTCC AGGGTGACGA     5940

TATGGTCATC TTCCTCCCCG AGGGCGCGCG CAGCGCGGCA CTCAAGTGGA CCCCCGCCGA     6000

GGTGGGCTTG TTTGGCTTCC ACATCCCGGT GAAGCACGTG AGCACCCCTA CCCCCAGCTT     6060

CTGCGGGCAC GTCGGCACCG CGGCCGGCCT CTTCCATGAT GTCATGCACC AGGCGATCAA     6120

GGTGCTTTGC CGCCGTTTCG ACCCAGACGT GCTTGAAGAA CAGCAGGTGG CCCTCCTCGA     6180

CCGCCTCCGG GGGGTCTACG CGGCTCTGCC TGACACCGTT GCCGCCAATG CTGCGTACTA     6240

CGACTACAGC GCGGAGCGCG TCCTCGCTAT CGTGCGCGAA CTTACCGCGT ACGCGCGGGG     6300

GCGCGGCCTC GACCACCCGG CCACCATCGG CGCGCTCGAG GAGATTCAGA CCCCCTACGC     6360

GCGCGCCAAT CTCCACGACG CCGACTAACG CCCCTGTACG TGGGGCCTTT AATCTTACCT     6420

ACTCTAACCA GGTCATCACC CACCGTTGTT TCGCCGCATC TGGTGGGTAC CCAACTTTTG     6480

CCATTCGGGA GAGCCCCAGG GTGCCCGAAT GGCTTCTACT ACCCCCATCA CCATGGAGGA     6540

CCTCCAGAAG GCCCTCGAGG CACAATCCCG CGCCCTGCGC GCGGAACTCG CCGCCGGCGC     6600

CTCGCAGTCG CGCCGGCCGC GGCCGCCGCG ACAGCGCGAC TCCAGCACCT CCGGAGATGA     6660

CTCCGGCCGT GACTCCGGAG GGCCCCGCCG CCGCCGCGGC AACCGGGGCC GTGGCCAGCG     6720

CAGGGACTGG TCCAGGGCCC CGCCCCCCCC GGAGGAGCGG CAAGAAACTC GCTCCCAGAC     6780

TCCGGCCCCG AAGCCATCGC GGGCGCCGCC ACAACAGCCT CAACCCCCGC GCATGCAAAC     6840

CGGGCGTGGG GGCTCTGCCC CGCGCCCCGA GCTGGGCCA CCGACCAACC CGTTCCAAGC      6900

AGCCGTGGCG CGTGGCCTGC GCCCGCCTCT CCACGACCCT GACACCGAGG CACCCACCGA     6960

GGCCTGCGTG ACCTCGTGGC TTTGGAGCGA GGGCGAAGGC GCGGTCTTTT ACCGCGTCGA     7020

CCTGCATTTC ACCAACCTGG GCACCCCCCC ACTCGACGAG GACGGCCGCT GGGACCCTGC     7080

GCTCATGTAC AACCCTTGCG GGCCCGAGCC GCCCGCTCAC GTCGTCCGCG CGTACAATCA     7140

ACCTGCCGGC GACGTCAGGG GCGTTTGGGG TAAAGGCGAG CGCACCTACG CCGAGCAGGA     7200

CTTCCGCGTC GGCGGCACGC GCTGGCACCG ACTGCTGCGC ATGCCAGTGC GCGGCCTCGA     7260

CGGCGACAGC GCCCCGCTTC CCCCCCACAC CACCGAGCGC ATTGAGACCC GCTCGGCGCG     7320

CCATCCTTGG CGCATCCGCT TCGGTGCCCC CCAGGCCTTC CTTGCCGGGC TCTTGCTCGC     7380

CACGGTCGCC GTTGGCACCG CGCGCGCCGG GCTCCAGCCC CGCGCTGATA TGGCGGCACC     7440

TCCTACGCTG CCGCAGCCCC CCTGTGCGCA CGGGCAGCAT TACGGCCACC ACCACCATCA     7500

GCTGCCGTTC CTCGGGCACG ACGGCCATCA TGGCGGCACC TTGCGCGTCG GCCAGCATTA     7560

CCGAAACGCC AGCGACGTGC TGCCCGGCCA CTGGCTCCAA GGCGGCTGGG GTTGCTACAA     7620
```

-continued

```
CCTGAGCGAC TGGCACCAGG GCACTCATGT CTGTCATACC AAGCACATGG ACTTCTGGTG    7680

TGTGGAGCAC GACCGACCGC CGCCCGCGAC CCCGACGCCT CTCACCACCG CGGCGAACTC    7740

CACGACCGCC GCCACCCCCG CCACTGCGCC GGCCCCCTGC CACGCCGGCC TCAATGACAG    7800

CTGCGGCGGC TTCTTGTCTG GGTGCGGGCC GATGCGCCTG CGCCACGGCG CTGACACCCG    7860

GTGCGGTCGG TTGATCTGCG GGCTGTCCAC CACCGCCCAG TACCCGCCTA CCCGGTTTGG    7920

CTGCGCTATG CGGTGGGGCC TTCCCCCCTG GGAACTGGTC GTCCTTACCG CCCGCCCCGA    7980

AGACGGCTGG ACTTGCCGCG GCGTGCCCGC CCATCCAGGC GCCCGCTGCC CCGAACTGGT    8040

GAGCCCCATG GGACGCGCGA CTTGCTCCCC AGCCTCGGCC CTCTGGCTCG CCACAGCGAA    8100

CGCGCTGTCT CTTGATCACG CCCTCGCGGC CTTCGTCCTG CTGGTCCCGT GGGTCCTGAT    8160

ATTTATGGTG TGCCGCCGCG CCTGTCGCCG CCGCGGCGCC GCCGCCGCCC TCACCGCGGT    8220

CGTCCTGCAG GGGTACAACC CCCCCGCCTA TGGCGAGGAG GCTTTCACCT ACCTCTGCAC    8280

TGCACCGGGG TGCGCCACTC AAGCACCTGT CCCCGTGCGC CTCGCTGGCG TCCGTTTTGA    8340

GTCCAAGATT GTGGACGGCG GCTGCTTTGC CCCATGGGAC CTCGAGGCCA CTGGAGCCTG    8400

CATTTGCGAG ATCCCCACTG ATGTCTCGTG CGAGGGCTTG GGGGCCTGGG TACCCGCAGC    8460

CCCTTGCGCG CGCATCTGGA ATGGCACACA GCGCGCGTGC ACCTTCTGGG CTGTCAACGC    8520

CTACTCCTCT GGCGGGTACG CGCAGCTGGC CTCTTACTTC AACCCTGGCG GCAGCTACTA    8580

CAAGCAGTAC CACCCTACCG CGTGCGAGGT TGAACCTGCC TTCGGACACA GCGACGCGGC    8640

CTGCTGGGGC TTCCCCACCG ACACCGTGAT GAGCGTGTTC GCCCTTGCTA GCTACGTCCA    8700

GCACCCTCAC AAGACCGTCC GGGTCAAGTT CCATACAGAG ACCAGGACCG TCTGGCAACT    8760

CTCCGTTGCC GGCGTGTCGT GCAACGTCAC CACTGAACAC CCGTTCTGCA ACACGCCGCA    8820

CGGACAACTC GAGGTCCAGG TCCCGCCCGA CCCCGGGGAC CTGGTTGAGT ACATTATGAA    8880

TTACACCGGC AATCAGCAGT CCCGGTGGGG CCTCGGGAGC CCGAATTGCC ACGGCCCCGA    8940

TTGGGCCTCC CCGGTTTGCC AACGCCATTC CCCTGACTGC TCGCGGCTTG TGGGGCCAC    9000

GCCAGAGCGC CCCCGGCTGC GCCTGGTCGA CGCCGACGAC CCCCTGCTGC GCACTGCCCC    9060

TGGACCCGGC GAGGTGTGGG TCACGCCTGT CATAGGCTCT CAGGCGCGCA AGTGCGGACT    9120

CCACATACGC GCTGGACCGT ACGGCCATGC TACCGTCGAA ATGCCCGAGT GGATCCACGC    9180

CCACACCACC AGCGACCCCT GGCATCCACC GGGCCCCTTG GGGCTGAAGT TCAAGACAGT    9240

TCGCCCGGTG GCCCTGCCAC GCACGTTAGC GCCACCCCGC AATGTGCGTG TGACCGGGTG    9300

CTACCAGTGC GGTACCCCCG CGCTGGTGGA AGGCCTTGCC CCCGGGGGAG GCAATTGCCA    9360

TCTCACCGTC AATGGCGAGG ACCTCGGCGC CGTCCCCCCT GGGAAGTTCG TCACCGCCGC    9420

CCTCCTCAAC ACCCCCCCGC CCTACCAAGT CAGCTGCGGG GGCGAGAGCG ATCGCGCGAC    9480

CGCGCGGGTC ATCGACCCCG CCGCGCAATC GTTTACCGGC GTGGTGTATG GCACACACAC    9540

CACTGCTGTG TCGGAGACCC GGCAGACCTG GCGGAGTGG GCTGCTGCCC ATTGGTGGCA    9600

GCTCACTCTG GGCGCCATTT GCGCCCTCCC ACTCGCTGGG TTACTCGCTT GCTGTGCCAA    9660

ATGCTTGTAC TACTTGCGCG GCGCTATAGC GCCTCGCTAG TGGGCCCCCG CGCGAAACCC    9720

GCACTAGGCC ACTAGATCCC CGCACCTGTT GCTGTATAG                         9759
```

(2) INFORMATION FOR SEQ ID NO:2:

(i) SEQUENCE CHARACTERISTICS:
        (A) LENGTH: 1727 base pairs
        (B) TYPE: nucleic acid

```
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:
```

| | | | | | |
|---|---|---|---|---|---|
| CAATGGAAGC | TATCGGACCT | CGCTTAGGAC | TCCCATTCCC | ATGGAGAAGC | TCCTAGATGA | 60
| GGTTCTTGCC | CCCGGTGGGC | CTTATAACTT | AACCGTCGGC | AGTTGGGTAA | GAGACCACGT | 120
| CCGATCAATT | GTCGAGGGCG | CGTGGGAAGT | GCGCGATGTT | GTTACCGCTG | CCCAAAAGCG | 180
| GGCCATCGTA | GCCGTGATAC | CCAGACCTGT | GTTCACGCAG | ATGCAGGTCA | GTGATCACCC | 240
| AGCACTCCAC | GCAATTTCGC | GGTATACCCG | CCGCCATTGG | ATCGAGTGGG | GCCCTAAAGA | 300
| AGCCCTACAC | GTCCTCATCG | ACCCAAGCCC | GGGCCTGCTC | CGCGAGGTCG | CTCGCGTTGA | 360
| GCGCCGCTGG | GTCGCACTGT | GCCTCCACAG | GACGGCACGC | AAACTCGCCA | CCGCCCTGGC | 420
| CGAGACGGCC | GGCGAGGCGT | GGCACGCTGA | CTACGTGTGC | GCGCTGCGTG | GCGCACCGAG | 480
| CGGCCCCTTC | TACGTCCACC | CTGAGGACGT | CCCGCACGGC | GGTCGCGCCG | TGGCGGACAG | 540
| ATGCTTGCTC | TACTACACAC | CCATGCAGAT | GTGCGAGCTG | ATGCGTACCA | TTGACGCCAC | 600
| CCTGCTCGTG | GCGGTTGACT | TGTGGCCGGT | CGCCCTTGCG | GCCCACGTCG | GCGACGACTG | 660
| GGACGACCTG | GCATTGCCT | GGCATCTCGA | CCATGACGGC | GGTTGCCCCG | CCGATTGCCG | 720
| CGGAGCCGGC | GCTGGGCCCA | CGCCCGGCTA | CACCCGCCCC | TGCACCACAC | GCATTTACCA | 780
| AGTCCTGCCG | GACACCGCCC | ACCCCGGGCG | CCTCTACCGG | TGCGGGCCCC | GCCTGTGGAC | 840
| GCGCGATTGC | GCCGTGGCCG | AACTCTCATG | GGAGGTTGCC | CAACACTGCG | GGCACCAGGC | 900
| GCGCGTGCGC | GCCGTGCGAT | GCACCCTCCC | TATCCGCCAC | GTGCGCAGCC | TCCAACCCAG | 960
| CGCGCGGGTC | CGACTCCCGG | ACCTCGTCCA | TCTCGCCGAG | GTGGGCCGGT | GGCGGTGGTT | 1020
| CAGCCTCCCC | CGCCCCGTGT | TCCAGCGCAT | GCTGTCCTAC | TGCAAGACCC | TGAGCCCCGA | 1080
| CGCGTACTAC | AGCGAGCGCG | TGTTCAAGTT | CAAGAACGCC | CTGAGCCACA | GCATCACGCT | 1140
| CGCGGGCAAT | GTGCTGCAAG | AGGGGTGGAA | GGGCACGTGC | GCCGAGGAAG | ACGCGCTGTG | 1200
| CGCATACGTA | GCCTTCCGCG | CGTGGCAGTC | TAACGCCAGG | TTGGCGGGGA | TTATGAAAGG | 1260
| CGCGAAGCGC | TGCGCCGCCG | ACTCTTTGAG | CGTGGCCGGC | TGGCTGGACA | CCATTTGGGA | 1320
| CGCCATTAAG | CGGTTCTTCG | GTAGCGTGCC | CCTCGCCGAG | CGCATGGAGG | AGTGGGAACA | 1380
| GGACGCCGCG | GTCGCCGCCT | TCGACCGCGG | CCCCCTCGAG | GACGGCGGGC | GCCACTTGGA | 1440
| CACCGTGCAA | CCCCCAAAAT | CGCCGCCCCG | CCCTGAGATC | GCCGCGACCT | GGATCGTCCA | 1500
| CGCAGCCAGC | GCAGACCGCC | ATTGCGCGTG | CGCTCCCCGC | TGCGACGTCC | CGCGCGAACG | 1560
| TCCTTCCGCG | CCCGCCGGCC | CGCCGGATGA | CGAGGCGCTC | ATCCCGCCGT | GGCTGTTCGC | 1620
| CGAGCGCCGT | GCCCTCCGCT | GCCGCGAGTG | GGATTTCGAG | GCTCTCCGCG | CGCGCGCCGA | 1680
| TACGGCGGCC | GCGTCCGCCC | CGCTGGCTCC | CCGCCCCGCG | CGGTACC | | 1727

```
(2) INFORMATION FOR SEQ ID NO:3:

(i) SEQUENCE CHARACTERISTICS:
        (A) LENGTH: 2558 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (xi) SEQUENCE DESCRIPTION: SEQ ID NO:3:

```
GCTAGCCGCC GCGCGTCGGT GGGCGTGTGT CGCGTGCCCC CTCCTCGGCG CTGGCGTCTA    60
CGGCTGGTCT GCTGCGGAGT CCCTCCGAGC CGCGCTCGCG GCTACGCGCA CCGAGCCCGT   120
CGAGCGCGTG AGCCTGCACA TCTGCCACCC CGACCGCGCC ACGCTGACGC ACGCCTCCGT   180
GCTCGTCGGC GCGGGCTCG CTGCCAGGCG CGTCAGTCCT CCTCCGACCG AGCCCCTCGC    240
ATCTTGCCCC GCCGGTGACC CGGGCCGACC GGCTCAGCGC AGCGCGTCGC CCCCAGCGAC   300
CCCCCTTGGG GATGCCACCG CGCCCGAGCC CCGCGGATGC CAGGGGTGCG AACTCTGCCG   360
GTGCACGCGC GTCACCAATG ACCGCGCCTA TGTCAACCTG TGGCTCGAGC GCGACCGCGG   420
CGCCACCAGC TGGGCCATGC GCATTCCCGA GGTGGTTGTC TACGGGCCGG AGCACCTCGC   480
CACGCATTTT CCATTAAACC ACTACAGTGT GCTCAAGCCC GCGGAGGTCA GGCCCCCGCG   540
AGGCATGTGC GGGAGTGACA TGTGGCGCTG CCGCGGCTGG CATGGCATGC CGCAGGTGCG   600
GTGCACCCCC TCCAACGCTC ACGCCGCCCT GTGCCGCACA GGCGTGCCCC CTCGGGCGAG   660
CACGCGAGGC GGCGAGCTAG ACCCAAACAC CTGCTGGCTC CGCGCCGCCG CCAACGTTGC   720
GCAGGCTGCG CGCGCCTGCG GCGCCTACAC GAGTGCCGGG TGCCCCAAGT GCGCCTACGG   780
CCGCGCCCTG AGCGAAGCCC GCACTCATGA GGACTTCGCC GCGCTGAGCC AGCGGTGGAG   840
CGCGAGCCAC GCCGATGCCT CCCCTGACGG CACCGGAGAT CCCCTCGACC CCTGATGGA    900
GACCGTGGGA TGCACCTGTT CGCGCGTGTG GGTCGGCTCC GAGCATGAGG CCCCGCCCGA   960
CCAACTCCTG GTGTCCCTTC ACCGTGCCCC AAATGGTCCG TGGGCGTAG TGCTCGAGGT   1020
GCGTGCGCGC CCCGAGGGGG GCAACCCCAC CGGCCACTTC GTCTGCGCGG TCGGCGGCGG   1080
CCCACGCCGC GTCTCGGACC GCCCCCACCT CTGGCTTGCG GTCCCCCTGT CTCGGGGCGG   1140
TGGCACCTGT GCCGCGACCG ACGAGGGGCT GGCCCAGGCG TACTACGACG ACCTCGAGGT   1200
GCGCCGCCTC GGGGATGACG CCATGGCCCG GGCGGCCCTC GCATCAGTCC AACGCCCTCG   1260
CAAAGGCCCT TACAATATCA GGGTATGGAA CATGGCCGCA GGCGCTGGCA AGACTACCCG   1320
CATCCTCGCT GCCTTCACGC GCGAAGACCT TTACGTCTGC CCCACCAATG CGCTCCTGCA   1380
CGAGATCCAG GCCAAACTCC GCGCGCGCGA TATCGACTTC AAGAACGCCG CCACCTACGA   1440
GCGCCGGCTG ACGAAACCGC TCGCCGCCTA CCGCCGCATC TACATCGATG AGGCGTTCAC   1500
TCTCGGCGGC GAGTACTGCG CGTTCGTTGC CAGCCAAACC ACCGCGGAGG TGATCTGCGT   1560
CGGTGATCGG GACCAGTGCG GCCCACACTA CGCCAATAAC TGCCGCACCC CCGTCCCTGA   1620
CCGCTGGCCT ACCGAGAGCT CACGCCACAC TTGGCGCTTC CCCGACTGCT GGGCGGCCCG   1680
CCTGCGCGCG GGGCTCGATT ATGACATCGA GGGCGAGCGC ACCGGCACCT TCGCCTGCAA   1740
CCTTTGGGAC GGCCGCCAGG TCGACCTTCA CCTCGCCTTC TCGCGCGAAA CCGTGCGCCG   1800
CCTTCACGAG GCTGGCATAC GCGCATACAC CGTGCGCGAG GCCAGGGTA TGAGCGTCGG   1860
CACCGCCTGC ATCCATGTAG GCAGAGACGG CACGGACGTT GCCCTGGCGC TGACACGCGA   1920
CCTCGCCATC GTCAGCCTGA CCCGGGCCTC CGACGCACTC TACCTCCACG AGCTCGAGGA   1980
CGGCTCACTG CGCGCTGCGG GGCTCAGCGC GTTCCTCGAC GCCGGGGCAC TGGCGGAGCT   2040
CAAGGAGGTT CCCGCTGGCA TTGACCGCGT TGTCGCCGTC GAGCAGGCAC CACCACCGTT   2100
GCCGCCCGCC GACGGCATCC CCGAGGCCCA AGACGTGCCG CCCTTCTGCC CCGCACTCT   2160
```

```
GGAGGAGCTC GTCTTCGGCC GTGCCGGCCA CCCCCATTAC GCGGACCTCA ACCGCGTGAC    2220

TGAGGGCGAA CGAGAAGTGC GGTACATGCG CATCTCGCGT CACCTGCTCA ACAAGAATCA    2280

CACCGAGATG CCCGGAACGG AACGCGTTCT CAGTGCCGTT TGCGCCGTGC GGCGCTACCG    2340

CGCGGGCGAG GATGGGTCGA CCCTCCGCAC TGCTGTGGCC CGCCAGCACC CGCGCCCTTT    2400

TCGCCAGATC CCACCCCCGC GCGTCACTGC TGGGGTCGCC CAGGAGTGGC GCATGACGTA    2460

CTTGCGGGAA CGGATCGACC TCACTGATGT CTACACGCAG ATGGGCGTGG CCGCGCGGGA    2520

GCTCACCGAC CGCTACGCGC GCCGCTATCC TGAGATCT                            2558
```

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

```
GGGAAGCTTG CACGACACGG ACAAAAGCC                                        29
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

```
TAGTCTTCGG CGCAAGG                                                     17
```

(2) INFORMATION FOR SEQ ID NO:6:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

```
CGCGAATTCT TTTTTTTTTT TTTTTTTTTC TATACAGCAA CAGGTGC                    47
```

(2) INFORMATION FOR SEQ ID NO:7:

(i) SEQUENCE CHARACTERISTICS:
        (A) LENGTH: 55 base pairs
        (B) TYPE: nucleic acid
        (C) STRANDEDNESS: single
        (D) TOPOLOGY: linear -continued (ii) MOLECULE TYPE: cDNA (iii) HYPOTHETICAL: NO (iv) ANTI-SENSE: NO (xi) SEQUENCE DESCRIPTION: SEQ ID NO:7:

TCGAAGCTTA TTTAGGTGAC ACTATAGCAA TGGAAGCTAT CGGACCTCGC TTAGG              55

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

TTTGCCAACG CCACGGC                                                       17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

AGCTCACCGA CCGCTAC                                                       17

HIGHLY INFECTIOUS RUBELLA VIRUS CLONES AND METHODS OF PRODUCTION

CROSS-REFERENCE TO RELATED APPLICATIONS

This is a continuation-in-part of U.S. patent application Ser. No. 08/459,041 filed Jun. 2, 1995, now U.S. Pat. No. 5,663,065, which is a continuation-in-part of U.S. patent application Ser. No. 08/093,453, filed Jul. 19, 1993, now U.S. Pat. No. 5,439,814, which is a continuation of U.S. patent application Ser. No. 07/722,334, filed on Jun. 28, 1991, now abandoned.

The U.S. Government has rights in this invention arising out of National Institutes of Health (NIAID) grant number AI21389.

The present invention relates to the field of molecular virology and more particularly to construction of highly infectious rubella virus cDNA clones.

BACKGROUND OF THE INVENTION

Rubella virus is a major human pathogen. Infection with rubella virus can cause serious birth defects and chronic disease. There was a mini-epidemic of both rubella and congenital rubella syndrome in the United States between 1989 and 1991.

Rubella was first described in the eighteenth century in Germany. The symptoms of a rash and mild fever were similar to those of measles, so the disease was given the name German measles. The name "rubella" was coined in 1814 when physicians realized that the disease was unique and was not merely a variant of scarlatina (scarlet fever) or rubeola (measles).

Rubella is a relatively harmless disease in young children. However, during the first trimester of pregnancy, rubella virus infection can cause fetal death. If the fetus survives, it may be born deaf or have cataracts, cardiac abnormalities, microcephaly, motor deficits or other congenital anomalies. The infant may also be born with thrombocytopenic purpura, hepatosplenomegaly, icterus, anemia, and low birth weight. The presence of one or more of these defects has been termed "congenital rubella syndrome" or CRS.

The rubella virus was isolated in 1962 at the beginning of a worldwide rubella epidemic which lasted from 1962 to 1965. This epidemic peaked in the United States in 1964, resulting in the birth of approximately 20,000 infants exhibiting congenital rubella syndrome.

Scientists began development of an effective vaccine against the rubella virus during the rubella epidemic. Effective attenuated vaccines became available in the late 1960's and are still used today. These attenuated vaccines are live viruses that have been passaged to reduce their virulence. Attenuated vaccines produce immunity, but can cause disease. Protection is believed to persist for at least 15 years after inoculation with the attenuated rubella vaccine.

Various vaccination schedules have been set up in different parts of the world to eliminate rubella infection, especially of the human fetus. The rubella immunization program established in Great Britain requires vaccination of all girls between the ages of 10 and 14. The United States immunization program vaccinates infants at approximately 15 months and requires a certificate of vaccination prior to attending school. The United States program is designed to eradicate the disease among the population that is most responsible for transmission of rubella, whereas the program of Great Britain seeks to achieve complete protection for those at risk for pregnancy. One disadvantage to the United States program is that protection against rubella may dissipate at the very time when immunity is most needed, namely, during the child-bearing years.

Vaccination of women of child-bearing age having undetectable antibody titers is recommended in both the United States and Great Britain. However, there are several risks to this procedure. First, there is a risk that these women may be pregnant and not be aware of their pregnancy, or they may become pregnant within a few months following immunization. Vaccination against rubella is contraindicated in pregnant women because the live virus in the vaccine can cross the placenta and infect the fetus. Pregnant women who have not previously been infected with the rubella virus or who have not been vaccinated prior to becoming pregnant are advised to refrain from becoming vaccinated during their pregnancy. These women are therefore at risk for contracting rubella by coming in contact with infectious persons, including those recently vaccinated with the attenuated vaccine.

Vaccination of older women has been associated with chronic arthritis and neurological symptoms. Scientists believe that these symptoms may be due to the persistent nature of the attenuated rubella virus in the currently available vaccines. Rubella virus is the sole member of the rubivirus genus of the Togavirus family. Compared to other viruses, very little is known about the molecular biology of the rubella virus. The rubella virion consists of single-stranded RNA encapsidated in an icosahedral nucleocapsid surrounded by a lipid envelope. Multiple copies of a viral protein, designated the C protein (MW=32,000–38,000 daltons), make up the nucleocapsid. Two types of viral glycoprotein, designated E1 and E2 (MW=53,000–58,000 daltons and 42,000–48,000 daltons, respectively), are embedded in the envelope, as reported by Waxham, M. N. and Wolinsky, J. S., *Virology* 126:194–203 (1983). The E2 glycoprotein has been further subdivided into two subgroups, designated E2a and E2b, by their ability to migrate differently when resolved by polyacrylamide gel electrophoresis, as described by Oker-Blom, C., et al., *J. Virol.* 46:964–973 (1983). E1- is the viral hemagglutinin. Neutralizing epitopes have been found on both E1 and E2 by Waxham, M. N. and Wolinsky, J. S., *Virology* 143:153–165 (1985) and Green, K. Y., and Dorsett, P. H., *J. Virol.*, 57:893–898 (1986).

The rubella virus genomic RNA is of positive polarity and is capped and polyadenylated. In infected cells, a second positive polarity RNA strand is synthesized to serve as messenger RNA for translation of structural proteins. This second strand is the first 3327 nucleotides beginning from the 3' end of the genomic RNA. The structural proteins are proteolytically processed from a polyprotein precursor during translation. The order of these proteins in the polyprotein is $NH_2$—C—E2—E1—COOH, as reported by Oker-Blom, C., et al. (1983); Oker-Blom, C., *J. Virol.* 51:354–358 (1984).

Recombinant vaccines are based on live microorganisms which have been genetically manipulated so that they are not pathogenic, but result in immunity against the virulent organism. Recombinant vaccines can only cause disease if a rare genetic mutation or recombinant event occurs which allows the microorganism to revert to wild type. A recombinant vaccine is generally safer and more effective than an attenuated vaccine because the engineered mutations remove or inactivate only specific portions of the genome, whereas attenuated vaccines contain random mutations. In order to develop a recombinant vaccine, one must first have the nucleic acid sequence of the entire viral genome, including both the information required for infection and at least limited replication of the virus, and for antigenicity. Once the entire sequence has been determined, a cDNA clone can be produced that is infectious and can be modified to be non-virulent.

An infectious cDNA clone is a complete DNA copy of an RNA virus genome contained in a vector, such as a plasmid, from which RNA transcripts of the genome can be synthesized in vitro. In the case of positive-polarity RNA viruses such as rubella, such transcripts are infectious when transfected into cells. The development of an infectious clone is a landmark event in the molecular biology of any RNA virus. Although an infectious clone for rubella virus has been described (Wang, et al., *J. Virol.* 68:3550–3557 (1994)), this cDNA clone displayed low infectivity (approximately 5 plaques/10 µg of transcripts). Increasing the infectivity of this clone would increase the efficiency of a recombinant attenuated rubella vaccine derived from the clone and would provide an improved molecular biology tool for studying rubella virus replication.

However, successful generation of highly infectious cDNA clones has often been problematic due to the presence of mutations in the virus RNA template population caused by the inherent mutability of RNA viruses, the relatively low fidelity of the DNA polymerases used in cDNA synthesis, instability and toxicity of viral sequences in bacterial hosts, and the infidelity of the RNA polymerases used for in vitro transcriptions. Therefore, it is clear that there remains a strong need for an infectious cDNA clone of the rubella virus genome having a higher infectivity than currently available rubella virus clones. The isolation of a highly infectious cDNA clone will be useful for the development of a rubella vaccine that can be safely administered to pregnant and older women without risk of birth defects, auto immune disease, or neurologic symptoms.

SUMMARY OF THE INVENTION

Highly infectious cDNA clones of the rubella virus are provided herein. The clones are chimeric constructs containing portions of both a cDNA clone having a low specific infectivity and a second rubella virus genome. The infectious rubella virus clones are useful as molecular biology tools for studying rubella virus and can be useful for developing recombinant vaccines against rubella.

The highly infectious cDNA clones have a specific infectivity greater than 0.5 plaques/µg of transcript. In several preferred embodiments of the invention, the specific infectivities of viral transcripts were approximately $10^4$ plaques/µg of transcript.

In the preferred embodiments, the cDNA clones are prepared by replacing one or more large fragments of a w-Therien-derived infectious cDNA clone with corresponding fragments from an f-Therien rubella virus strain.

It is therefore an object of the present invention to provide a highly infectious cDNA clone of the rubella virus genomic RNA.

It is a further object of the present invention to provide a molecular biology tool for studying rubella, particularly rubella virus replication.

It is a further object of the present invention to provide cDNA clones for the development of a recombinant rubella virus vaccine.

DETAILED DESCRIPTION OF THE INVENTION

Figure 1:
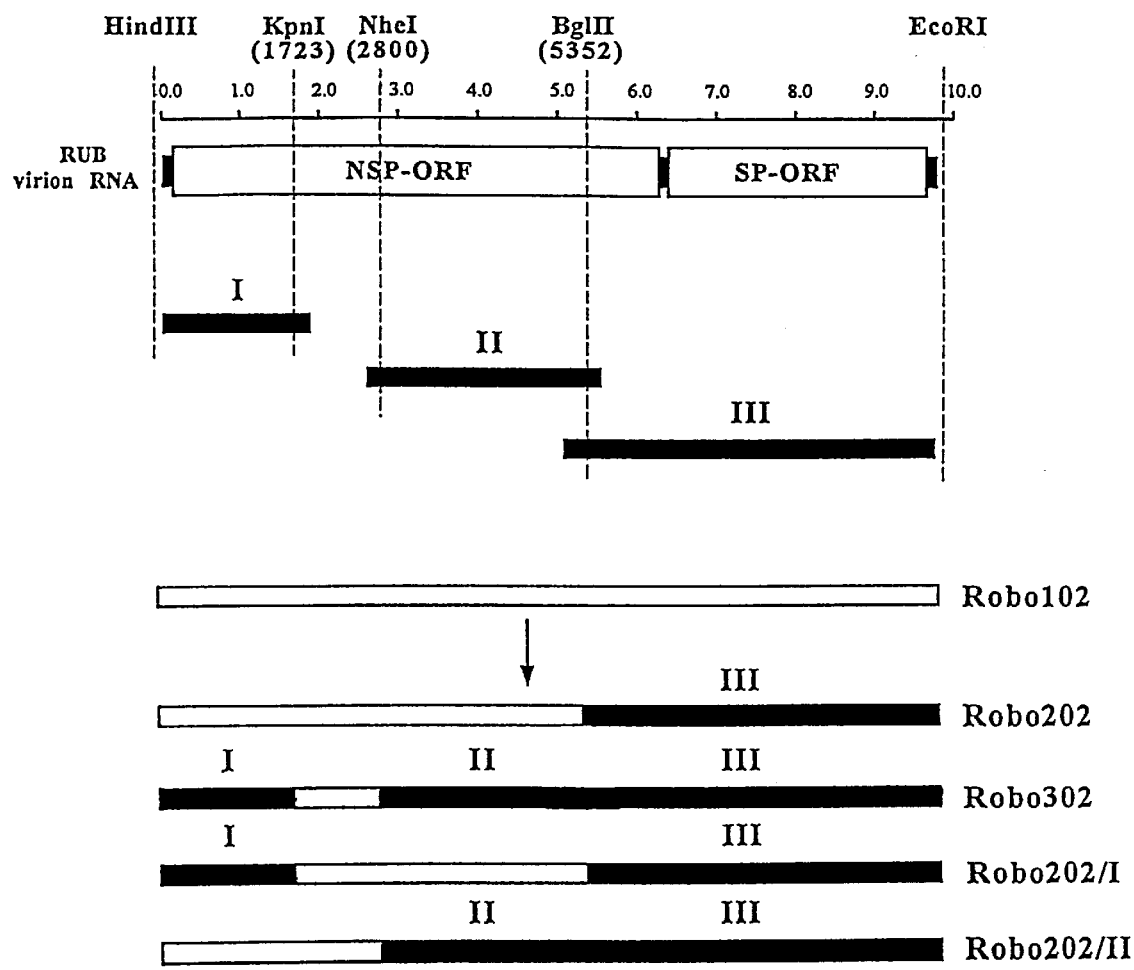
FIG. 1 is a schematic diagram showing modifications to the construct Robo102 to produce highly infectious clones, Robo202, Robo302, Robo202/I and Robo202/II.
Figure 2:
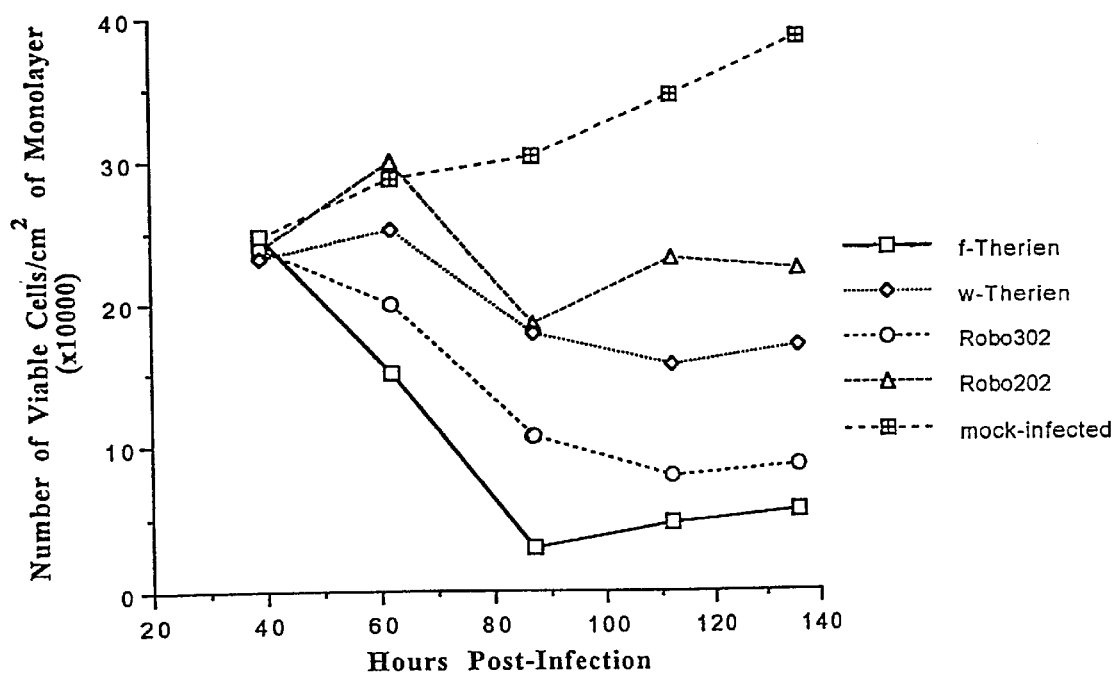
FIG. 2 is a graph comparing the infectivity of the Robo302 and Robo202 constructs with the f-Therien rubella virus strain, the w-Therien rubella virus strain, and a mock-infected control.

Highly infectious, isolated cDNA molecules or clones of rubella virus are described. The infectious rubella virus clones are useful as molecular biology tools for studying rubella virus and for developing recombinant vaccines against rubella.

The term "highly infectious cDNA clone" is defined herein as a cDNA clone having a specific infectivity of greater than 0.5 plaques/µg of transcript. The term "low infectivity" or "low-specific infectivity" is defined herein as a specific infectivity of less than or equal to 0.5 plaques/µg of transcript.

The highly infectious, isolated cDNA molecules are inserted into a vector that enables replication of the nucleotide sequence of the molecules. A preferred vector is a bacterial plasmid such as pUC 19, pGEM, or PBR-322 (all available from Promega Biotec, Madison, Wis.) or pC11921 adjacent to a bacteriophage RNA polymerase promoter sequence such as the SP6 RNA polymerase (Promega Biotec) such that RNA copies of the rubella virus DNA can be synthesized in vitro. The vector is chemically introduced into susceptible culture cells, for example, *E. coli*, for amplification and production of large amounts of the cDNA clone. For use, the purified infectious clone is restricted with a restriction endonuclease such as Nsi 1 (New England Biolabs, Beverly, Mass.) for linearization at the termination of the rubella virus cDNA sequences. The linearized plasmid is then transcribed with an RNA polymerase such as SP6 RNA polymerase, which results in production of RNA transcripts templated from the rubella virus cDNA sequence in the non-pathogenic infectious clone.

In preferred embodiments of the present invention, the rubella virus clones have specific infectivities of approximately $10^4$ plaques/µg of transcript. In these preferred embodiments, the rubella virus cDNA clones are chimeric constructs, which contain portions of both an infectious cDNA clone, having a low specific infectivity of approximately 0.5 plaques/ug of transcript or less, and portions, or fragments, of cDNA from a second rubella virus genome, in which the cDNA has a minimal number of deleterious mutations that adversely affect infectivity. The highly infectious constructs are prepared by replacing one or more portions of the cDNA clone having low infectivity with corresponding DNA fragments from the second rubella virus strain. The specific infectivities achieved by these cDNA clones exhibit an increase of at least $10^4$ fold over infectivity achieved using a cDNA clone derived solely from a w-Therien rubella virus strain.

In the most preferred embodiments of the present invention, the cDNA clone having a low specific infectivity is derived from the f-Therien rubella virus strain and the cDNA fragments used to replace portions of the cDNA clone are derived from the w-Therien rubella virus strain. Most preferably, the chimeric constructs contain one or more portions of the infectious cDNA clone Robo102, derived from the w-Therien rubella virus strain, as described in U.S. patent application Ser. No. 08/459,041, now U.S. Pat. No. 5,663,065, which is incorporated by reference herein, and one or more fragments of cloned cDNA derived from the f-Therien rubella virus strains.

Preferably, the cDNA fragments are created using the technique known by those skilled in the art as reverse transcriptase-long polymerase chain reaction (RT-long PCR) or high-fidelity long PCR, which allows for the amplification of long nucleic acid sequences. This use of this technique results in a reduction of the number of deleterious mutations in the genomic cDNA. High-fidelity long PCR amplification of rubella virus cDNA fragments is achieved with first strand cDNA synthesis, using currently available nucleic acid synthesis kits such as the RiboClone cDNA Synthesis System kit (Promega Corporation, Madison, Wis.) according to the protocol of the manufacturer, followed by PCR amplification. Exemplary oligonucleotide primers for the generation of nucleic acid fragments, with which to replace the portions of the cDNA clone having low infectivity, are set forth in the Examples below.

As shown in FIG. 1, in a first preferred embodiment of the present invention, the 5' end portion of the cDNA clone having low specific infectivity (the w-Therien derived Robo102 construct) is replaced with the corresponding cDNA fragment (fragment III) from a second rubella virus genome (the f-Therien strain of the rubella virus genome), to create a highly infectious construct (Robo202). Fragment III contains the entire structural protein open reading frame region (SP-ORF) of the genome. The structural protein open reading frame encodes at least three structural proteins, C, E1 and E2. Fragment III also contains a portion of the 5'-end of the non-structural protein open reading frame (NSP-ORF). Fragment III is also described as a nucleic acid molecule between restriction endonuclease cleavage sites EcoRI and BglII. More specifically, the Robo202 chimeric construct includes nucleotides 1 to approximately 5352 of SEQ ID NO. 1 and replaces nucleotides 5353 to 9734 of SEQ ID NO. 1 with the corresponding sequence from the f-Therien rubella virus genome.

In a second preferred embodiment of the present invention, two fragments from a second rubella virus genome (the f-Therien rubella virus genome), are used to replace the corresponding fragments of the infectious rubella virus cDNA clone having low specific infectivity (Robo102) to create a chimeric construct having high specific infectivity (Robo302). As shown in FIG. 1, the first fragment (fragment I) contains the 3' end of the non-structural open reading frame. Fragment I is also described as the nucleic acid molecule between restriction endonuclease cleavage sites HindIII and KpnI. The nucleic acid sequence of fragment I is set forth in the sequence listing as SEQ ID NO. 2. The second fragment (fragment II) contains the 5' end of the non-structural open reading frame and the entire structural protein open reading frame. Fragment II is also described as the nucleic acid molecule between restriction endonuclease cleavage sites NheI and BglII. The nucleic acid sequence of fragment II is set forth in the sequence listing as SEQ ID NO. 3. In particular, fragment I replaces nucleotides 1 to 1723 of Robo102, and fragment II replaces nucleotides 2800 to 5352 of Robo102. The resulting construct, Robo302, contains roughly 90% of the f-Therien rubella virus genome and 10% of the w-Therien strain of the rubella virus genome.

In a third preferred embodiment of the present invention, fragments I and III, as described above, replace the corresponding portions of the infectious cDNA clone having low infectivity (Robo102) to produce a highly infectious cDNA clone (Robo202/I). As shown in FIG. 1, the resulting cDNA construct contains both the 5' and 3' ends of the f-Therien strain of the rubella virus genome corresponding to nucleotides 1 to 1723 and 5352 to 9734, respectively. The central portion of the Robo202/I cDNA is derived from nucleotides 1723 to 5352 of the w-Therien strain.

In a fourth preferred embodiment of the present invention, fragments II and III, as described above, replace the corresponding portions of the infectious cDNA clone having low infectivity (Robo102) to produce a highly infectious cDNA clone (Robo202/II). As shown in FIG. 1, the resulting cDNA construct contains the 5' end of the w-Therien rubella virus genome up to nucleotide 2800 with the remaining section consisting of the f-Therien rubella virus genome.

The highly infectious rubella virus cDNA clones described above will be further understood with reference to the following non-limiting examples.

EXAMPLE 1

Preparation of f-Therien Virion RNA and RT-long PCR

Vero cells (ATCC, Rockville, Md.) were infected with f-Therien rubella virus (multiplicity of infection (m.o.i.)= 0.5). Four days post infection, culture medium was harvested and PEG-precipitated virion RNA was isolated using either TRI-Reagent LS (Molecular Research Center, Cincinnati, Ohio), according to the protocol provided by the manufacturer, or by using the method described by Wang, C. Y. et al., *J. Virol.* 68:3550–3557 (1994). The extracted RNA was further purified by oligo-(dT)-cellulose chromatography, redissolved in 50 μl of water, and stored at −70° C.

First strand cDNA synthesis was performed with AMV reverse transcriptase (RiboClone™ cDNA Synthesis Kit; Promega, Madison, Wis.), according to the protocol provided by the manufacturer, in the presence of sodium pyrophosphate with one of the following three primers:

SEQ ID NO. 4:

5'-GGGAAGCTT<u>GCACGACACGGACAAAAGCC</u>

(underlined sequence is complementary to nucleotides 1897–1916 of the rubella virus genome)

SEQ ID NO. 5:

5'-TAGTCTTCGGCGCAAGG (complementary to nucleotides 5744–5760 of the rubella virus genome)

SEQ ID NO. 6:

5'-CGCGAATTC (T)$_{20}$

<u>CTA<u>TACAGC</u>AACAGGTGC</u>(contains an EcoRI site (double underlined), a (dT)$_{20}$-stretch, and a sequence complementary to nucleotides 9740–9757 of the rubella virus genome (single underlined))

Three large cDNA clones were then generated using the PCR techniques described by Barnes, W. M., et al., *Proc. Natl. Acad. Sci. USA* 91:2216–2220 (1994) and Cheng, S., et al., *Proc. Natl. Acad. Sci. USA* 91:5695–5699 (1994), the teachings of which are incorporated by reference herein. The single-stranded products, Fragments I, II, and III, were phenol-chloroform extracted and precipitated twice with ethanol, first in the presence of 2M ammonium acetate and second in the presence of 0.3 M sodium acetate. The precipitates were redissolved in 10 μg of water and 2 to 5 μl were used in 50 μl PCR reactions that contained 2.5 units of ExTaq temperature stable DNA polymerase (TaKaRa LA PCR kit, Pan Vera Corp., Madison, Wis.), and the following three primers:

SEQ ID NO. 7:

5'-TCGAAGCTTATTTAGGTGACACTATAGCAATG GAAGCTATCGGACCTCGCTTAGG (contains a HindIII site (double underlined), the SP6 RNA polymerase promoter (dot underlined), and nucleotides 1–28 of the rubella virus genome (single underlined))

SEQ ID NO. 8:

5'-TTTGCCAACGCCACGGC (containing nucleotides 2600–2616 of the rubella virus genome)

SEQ ID NO. 9:

5'-AGCTCACCGACCGCTAC (containing nucleotides 5319–5335 of the rubella virus genome)

The following primers and amplification protocols were utilized: for fragment I, the primer set forth in SEQ ID NO. 7 served as a primer for 30 cycles of 20 seconds at 98° C., one second at 55° C. and three minutes at 70° C.; for fragment II, the primer set forth in SEQ ID NO. 8 served as a primer for 30 cycles of 20 seconds at 98° C., one second at 50° C., and five minutes at 70° C.; and for fragment III, the primer set forth in SEQ ID NO. 9 served as a primer for 30 cycles of 20 seconds at 98° C., one second at 52° C., and seven minutes at 68° C. These techniques were slightly modified by the addition of 10% DMSO to the PCR amplifications due to the high G+C content of the rubella genome. Roughly ten percent of the rubella virus genome between fragments I and II could not be amplified from the virion RNA, presumably due to peculiarities of secondary and or tertiary structure in this region.

Using standard recombinant DNA techniques, fragments I, II, and III were digested with the restriction enzymes HindIII and KpnI, NheI and BglII, or BglII and EcoRI, respectively, as described below, and individually ligated with Robo102 from which the corresponding fragment had been removed. Phenol-chloroform extracted and linearized constructs were transcribed in vitro as described in Pugachev, K. V., P. W. Mason, and T. K. Frey *Virology* 209:155–166 (1995), using SP6 RNA polymerase (Epicentre Technologies, Madison, Wis.) in the presence of a cap structure analog, and transfected into Vero cells using lipofectin-mediated techniques described by Rice et al., *New Biol.* 1:285–296 (1989).

Freshly linearized Robo plasmids in the presence of the m7G(5')ppp(5')G cap structure analog (New England Biolabs, Beverly, Mass.) were used in the transcription reactions in accordance with the method of Rice et al., *New Biol.* 1:285–296 (1989), with the modification that Opti-MEMI-reduced serum medium replaced phosphate buffered saline (PBS) during transfection. Transfected cells were incubated and tested for rubella induced cytopathic effects.

As shown in FIG. 1, the construct containing fragment III was designated Robo202, the construct containing fragments I, II and III was designated Robo302, the construct containing fragments I and III was designated Robo202/I, and the construct containing fragments II and III was designated Robo202/II.

TABLE I

Average Titers Produced by Therien Viruses and Robo Constructs

| Virus | Titer (pfu/ml) |
|---|---|
| f-Therien | $2.6 \times 10^7$ |
| w-Therien | $2.5 \times 10^7$ |
| f-Therien | $1.4 \times 10^7$ |
| f-Therien | $1 \times 10^7$ |
| f-Therien | $1.36 \times 10^6$ |
| f-Therien | $1.2 \times 10^7$ |

EXAMPLE 2

Construction and Specific Infectivity of Robo202

The specific infectivity of the rubella virus cDNA clone designated Robo202, as described above in Example 1, was determined as follows. After PCR amplification of fragment III, as described above, the fragment was digested with restriction enzymes BglII and EcoRI and ligated with a similarly digested Robo102 clone, as shown in FIG. 1. In vitro transcription of the newly constructed clone, Robo202, and subsequent transfection into Vero cells resulted a $10^4$-fold increase in infectivity as shown below in Table I. While the slightly infectious Robo102 clone did not induce cytopathic effects within eight days after transfection into Vero cells, insertion of fragment III into the Robo102 clone resulted in cytopathic effects within five days of transfection into Vero cells. However, insertion of either fragment I or II, individually, did not increase the infectivity of subsequently produced viral transcripts, and therefore the deleterious mutation that caused low infectivity of Robo102 is believed to be located in the region replaced by fragment III.

EXAMPLE 3

Construction and Specific Infectivity of Robo302

Following PCR amplification of fragments I and II, the fragments were digested with restriction enzymes HindIII and KpnI, and NheI and BglII, respectively. The fragments were simultaneously inserted into a Robo202 clone wherein the corresponding fragments had been removed, resulting in the Robo302 construct, as shown in FIG. 1. The addition of fragments I and II to the Robo202 construct, produced viral transcripts with an increased specific infectivity.

Vero cells grown in 24-well plates were infected with the indicated viruses at an m.o.i. of 2 pfu/cell. At indicated times post infection, cells were trypsinized, washed with PBS and stained with trypan blue. Three aliquots of each trypsinized cell suspension were counted. As shown in FIG. 2, viral transcripts derived from the Robo302 clone induced approximately 80% cell death over the control, whereas viral transcripts derived from the Robo202 clone resulted in approximately 40% cell death. These results also paralleled the results of plaque assays wherein the Robo302 clone displayed a clear plaque phenotype, and the Robo202 clone displayed an opaque plaque phenotype.

EXAMPLE 4

Construction and Specific Infectivity of Robo202/I and Robo202/II

Fragments I and II were excised from the Robo302 construct with the appropriate restriction enzymes, and introduced individually to produce the Robo202/I and Robo202/II constructs, respectively. Introduction of either fragment resulted in decreased plaque opacity, with Robo202/II producing the most clear plaques, slightly smaller than the plaques produced by Robo302.

EXAMPLE 5

Growth Kinetics of Robo Constructs

Figure 3:
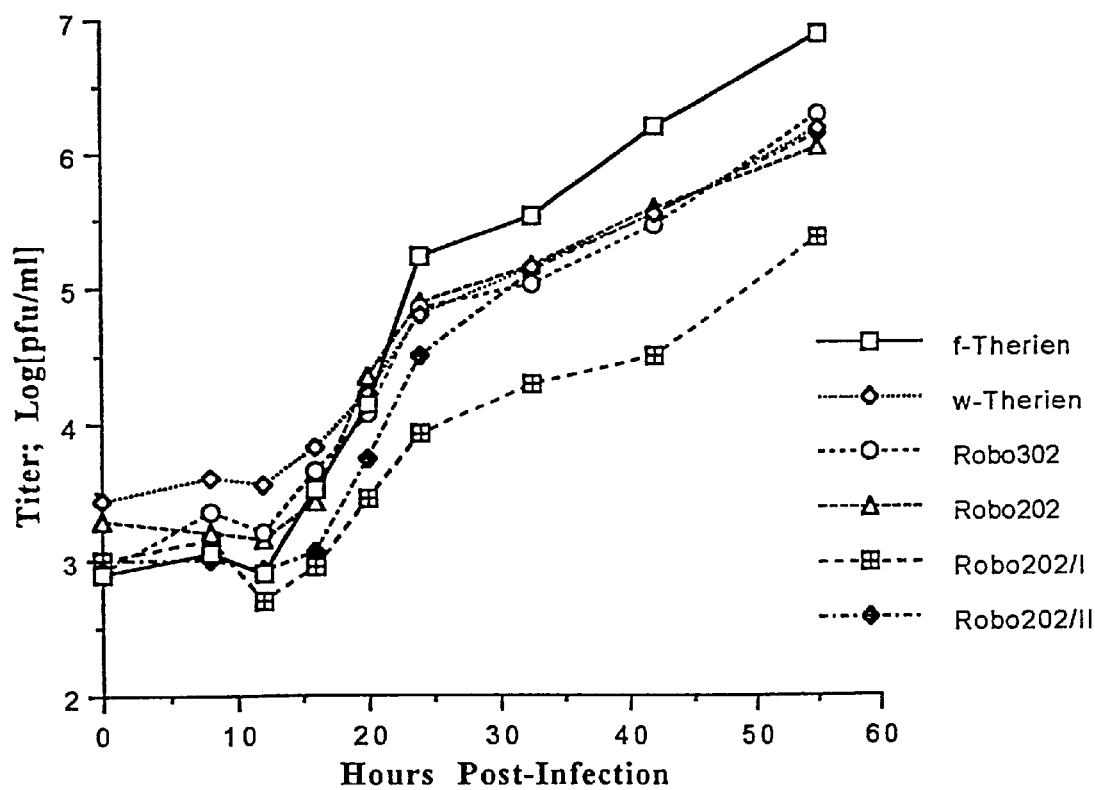
FIG. 3 is a graph comparing the growth curves of the two parent strains, w-Therien and f-Therien, with the four modified constructs, Robo202, Robo302, Robo202/I and Robo202/II, after infection of Vero cells at an m.o.i. of 2 pfu/cell. The graph shows average values of titers produced in two independent experiments.

To elucidate the basis of the difference in plaque phenotype between the Robo constructs, growth curves of the resulting viruses and their ability to kill infected cells were investigated. Because of the limited titer to which one of the viruses, Robo202/I, replicated, an m.o.i. of 2 pfu/cell was used in these experiments. As shown in FIG. 3, the growth kinetics of all of the viruses were similar with a lag phase of roughly 0–12 hours post infection, an exponential phase between 12 and 24 hours post infection, and a slower exponential phase through 55 hours post infection. While f-Therien produced the highest titers, w-Therien, Robo302, Robo202, and Robo202/II produced similar intermediate titers. Robo202/I virus grew to noticeably lower titers than the other viruses. Over a more prolonged course of infection (4 days), w-Therien titers caught up with f-Therien titers, Robo202, Robo302 and Robo202/II titers were approximately two fold lower than f- and w-Therien titers, whereas Robo202/I titers were 8–18 fold lower than any of the other viruses.

To analyze molecular differences between these viruses that could account for the difference in plaque morphology/cell killing, virus macromolecular synthesis was characterized. Production of the rubella virus-specific RNAs (of both positive and negative polarity) was examined by northern hybridization of total intracellular RNAs extracted from infected cells with the result that all of these viruses produced equivalent amounts of all the virus RNA species (data not shown). Non-structural and structural protein synthesis was analyzed by immunoprecipitation of the proteins from lysates of infected cells radiolabeled for 1.5 hours. As shown in FIG. 3, structural protein synthesis was similar for all of the viruses. However production of the non-structural proteins was higher in cells infected with the more cytopathic viruses (f-Therien and Robo302) than the less cytopathic viruses (w-Therien and Robo202). Robo 202/I also produced more non-structural proteins in comparison with Robo202/II. These differences were not due to differences in the number of infected cells in the culture since at 40 hours post infection, a similar percentage of cells (roughly 60%) was infected with f-Therien, w-Therien, Robo302, Robo202 and Robo202/II viruses as determined by indirect immunofluorescence. However, in Robo202/I infected cells, only 35% of cells were infected, probably due to the slower replication rate of this virus.

Modifications and variations of the DNA encoding an infectious rubella virus, method of making a less virulent rubella virus, an improved rubella virus vaccine and methods of use thereof will be obvious to those skilled in the art from the foregoing detailed description of the invention. Such modifications and variations are intended to come within the scope of the appended claims.

We claim:

1. A nucleic acid molecule having the nucleotide sequence set forth in SEQ ID NO:2.

2. A nucleic acid molecule having the nucleotide sequence set forth in SEQ ID NO:3.

* * * * *